US008758343B2

(12) United States Patent
Maughan et al.

(10) Patent No.: US 8,758,343 B2
(45) Date of Patent: Jun. 24, 2014

(54) BONE FIXATION APPARATUS

(75) Inventors: Thomas J. Maughan, Downingtown, PA (US); James P. Hearn, Coatesville, PA (US)

(73) Assignee: Depuy Synthes Products, LLC, Raynham, MA (US)

( * ) Notice: Subject to any disclaimer, the term of this patent is extended or adjusted under 35 U.S.C. 154(b) by 1062 days.

(21) Appl. No.: 11/116,051

(22) Filed: Apr. 27, 2005

(65) Prior Publication Data

US 2006/0247622 A1    Nov. 2, 2006

(51) Int. Cl.
*A61B 17/00* (2006.01)
*A61F 4/00* (2006.01)
*A61F 5/04* (2006.01)

(52) U.S. Cl.
USPC ............................................. 606/54; 606/59

(58) Field of Classification Search
USPC .......... 606/53–59, 61, 250, 279; 403/23, 131, 403/321, 322.19, 90, 91, 396
See application file for complete search history.

(56) References Cited

U.S. PATENT DOCUMENTS

| 2,767,003 | A | 10/1956 | Gilmont |
| 3,547,113 | A | 12/1970 | Swanson Gilmont |
| 3,727,610 | A | 4/1973 | Riniker |
| 3,961,854 | A | 6/1976 | Jaquet |
| 4,220,146 | A | 9/1980 | Cloutier |
| 4,244,360 | A | 1/1981 | Dohogne |
| 4,483,334 | A | 11/1984 | Murray |
| 4,502,473 | A | 3/1985 | Harris et al. |
| 4,547,092 | A | 10/1985 | Vetter et al. |
| 4,600,000 | A | 7/1986 | Edwards |
| 4,620,533 | A | 11/1986 | Mears |
| 4,628,919 | A | 12/1986 | Clyburn |
| 4,730,608 | A | 3/1988 | Schlein |
| 4,848,368 | A | 7/1989 | Kronner |
| 4,895,141 | A | 1/1990 | Koeneman et al. |
| 4,920,959 | A | 5/1990 | Witzel et al. |
| 4,941,481 | A | 7/1990 | Wagenknecht |
| 4,978,348 | A | 12/1990 | Ilizarov |
| 5,026,372 | A | 6/1991 | Sturtzkopf et al. |
| 5,047,029 | A | 9/1991 | Aebi et al. |
| 5,053,034 | A | 10/1991 | Olerud |

(Continued)

FOREIGN PATENT DOCUMENTS

| CN | 2496406 Y | 6/2002 |
| DE | 3139575 | 4/1983 |

(Continued)

OTHER PUBLICATIONS

International Search Report of PCT/US2006/015466, mailed Nov. 28, 2006.

*Primary Examiner* — Andrew Yang
(74) *Attorney, Agent, or Firm* — Fay Kaplun & Marcin, LLP

(57) ABSTRACT

A clamp assembly for bone fixation elements including first and second clamp structures configured to engage first and second bone fixation elements, respectively. The first clamp structure may have a first spherically contoured bearing surface. The second clamp structure may have a second spherically contoured bearing surface seated in sliding contact with the first bearing surface. A spring-loaded mechanism may apply a spring force urging the bearing surfaces together to resist pivotal movement of the clamp structures relative to each other. The clamp assembly may be used with an assembly of fixation elements to create an external fixation frame.

16 Claims, 13 Drawing Sheets

(56) References Cited

U.S. PATENT DOCUMENTS

| | | | |
|---|---|---|---|
| 5,074,866 A | 12/1991 | Sherman et al. | |
| 5,095,919 A | 3/1992 | Monticelli et al. | |
| 5,098,432 A | 3/1992 | Wagenknecht | |
| 5,122,140 A | 6/1992 | Asche et al. | |
| 5,152,280 A | 10/1992 | Danieli | |
| 5,160,335 A | 11/1992 | Wagenknecht | |
| 5,167,661 A | 12/1992 | Wagenknecht | |
| 5,219,349 A | 6/1993 | Krag et al. | |
| 5,275,599 A | 1/1994 | Zbikowski et al. | |
| 5,304,177 A | 4/1994 | Pennig | |
| 5,312,402 A | 5/1994 | Schlapfer et al. | |
| 5,312,403 A | 5/1994 | Frigg | |
| 5,314,426 A | 5/1994 | Pohl et al. | |
| 5,320,622 A | 6/1994 | Faccioli et al. | |
| 5,320,623 A | 6/1994 | Pennig | |
| 5,342,360 A | 8/1994 | Faccioli et al. | |
| 5,376,090 A | 12/1994 | Pennig | |
| 5,380,322 A | 1/1995 | van den Brink et al. | |
| 5,393,161 A | 2/1995 | Mata et al. | |
| 5,403,313 A | 4/1995 | Lin | |
| 5,405,347 A | 4/1995 | Lee et al. | |
| RE34,985 E | 6/1995 | Pennig | |
| 5,429,637 A | 7/1995 | Hardy | |
| 5,437,669 A * | 8/1995 | Yuan et al. | 606/61 |
| 5,439,465 A | 8/1995 | Tumibay | |
| 5,443,464 A | 8/1995 | Russell et al. | |
| 5,454,810 A | 10/1995 | Pohl et al. | |
| 5,498,262 A | 3/1996 | Bryan | |
| 5,501,544 A | 3/1996 | Cairns | |
| 5,545,162 A | 8/1996 | Huebner | |
| 5,591,164 A | 1/1997 | Nazre et al. | |
| 5,624,440 A * | 4/1997 | Huebner | 606/59 |
| 5,630,815 A | 5/1997 | Pohl et al. | |
| 5,643,258 A * | 7/1997 | Robioneck et al. | 606/54 |
| 5,653,707 A | 8/1997 | Taylor et al. | |
| 5,658,283 A | 8/1997 | Huebner | |
| 5,662,648 A | 9/1997 | Faccioli et al. | |
| 5,662,649 A | 9/1997 | Huebner | |
| 5,662,650 A | 9/1997 | Bailey et al. | |
| 5,674,221 A | 10/1997 | Hein et al. | |
| 5,676,664 A | 10/1997 | Allard et al. | |
| 5,681,309 A | 10/1997 | Ross, Jr. et al. | |
| 5,683,389 A | 11/1997 | Orsak | |
| 5,688,271 A | 11/1997 | Faccioli et al. | |
| 5,690,633 A | 11/1997 | Taylor et al. | |
| 5,702,389 A | 12/1997 | Taylor et al. | |
| 5,702,394 A | 12/1997 | Henry et al. | |
| 5,709,681 A | 1/1998 | Pennig | |
| 5,725,526 A | 3/1998 | Allard et al. | |
| 5,728,096 A | 3/1998 | Faccioli et al. | |
| 5,738,684 A | 4/1998 | Thomas et al. | |
| 5,741,252 A | 4/1998 | Mazzio et al. | |
| 5,743,898 A | 4/1998 | Bailey et al. | |
| 5,746,741 A | 5/1998 | Kraus et al. | |
| 5,752,953 A | 5/1998 | Slocum | |
| 5,752,954 A | 5/1998 | Mata et al. | |
| 5,766,173 A | 6/1998 | Ross, Jr. et al. | |
| 5,769,851 A | 6/1998 | Veith | |
| 5,785,709 A | 7/1998 | Kummer et al. | |
| 5,788,695 A | 8/1998 | Richardson | |
| 5,797,908 A | 8/1998 | Meyers et al. | |
| 5,803,924 A | 9/1998 | Oni et al. | |
| 5,810,814 A | 9/1998 | Newson | |
| 5,827,282 A | 10/1998 | Pennig | |
| 5,827,284 A | 10/1998 | Weigum et al. | |
| 5,843,081 A | 12/1998 | Richardson | |
| 5,863,292 A | 1/1999 | Tosic | |
| 5,885,282 A | 3/1999 | Szabo | |
| 5,891,144 A | 4/1999 | Mata et al. | |
| 5,897,555 A | 4/1999 | Clyburn et al. | |
| 5,921,985 A | 7/1999 | Ross, Jr. et al. | |
| 5,928,230 A | 7/1999 | Tosic | |
| 5,941,877 A | 8/1999 | Viegas et al. | |
| 5,941,879 A | 8/1999 | Walulik et al. | |
| 5,951,556 A | 9/1999 | Faccioli et al. | |
| 5,961,515 A | 10/1999 | Taylor et al. | |
| 5,968,043 A | 10/1999 | Ross, Jr. et al. | |
| 5,976,133 A | 11/1999 | Kraus et al. | |
| 5,976,134 A | 11/1999 | Huebner | |
| 5,997,537 A | 12/1999 | Walulik | |
| 6,007,534 A | 12/1999 | Gonzalez et al. | |
| 6,010,501 A | 1/2000 | Raskin et al. | |
| 6,022,348 A | 2/2000 | Spitzer | |
| 6,024,745 A | 2/2000 | Faccioli et al. | |
| 6,036,691 A | 3/2000 | Richardson | |
| 6,080,153 A | 6/2000 | Mata et al. | |
| 6,102,911 A | 8/2000 | Faccioli et al. | |
| 6,129,727 A | 10/2000 | Austin et al. | |
| 6,152,925 A | 11/2000 | Marsh et al. | |
| 6,162,223 A * | 12/2000 | Orsak et al. | 606/59 |
| 6,162,224 A | 12/2000 | Huebner | |
| 6,171,307 B1 | 1/2001 | Orlich | |
| 6,171,308 B1 | 1/2001 | Bailey et al. | |
| 6,171,309 B1 | 1/2001 | Huebner | |
| 6,176,860 B1 * | 1/2001 | Howard | 606/54 |
| 6,203,548 B1 | 3/2001 | Helland | |
| 6,217,577 B1 * | 4/2001 | Hofmann | 606/57 |
| 6,221,072 B1 | 4/2001 | Termaten | |
| 6,235,029 B1 | 5/2001 | Faccioli et al. | |
| 6,245,071 B1 * | 6/2001 | Pierson | 606/58 |
| 6,277,118 B1 | 8/2001 | Grant et al. | |
| 6,277,119 B1 | 8/2001 | Walulik et al. | |
| 6,340,361 B1 | 1/2002 | Kraus et al. | |
| 6,342,054 B1 | 1/2002 | Mata | |
| 6,355,037 B1 | 3/2002 | Crosslin | |
| 6,402,749 B1 | 6/2002 | Ashman | |
| 6,409,729 B1 | 6/2002 | Martinelli et al. | |
| 6,423,061 B1 | 7/2002 | Bryant | |
| 6,428,540 B1 | 8/2002 | Claes et al. | |
| 6,461,358 B1 | 10/2002 | Faccioli et al. | |
| 6,482,206 B2 | 11/2002 | Schoenefeld | |
| 6,491,694 B1 | 12/2002 | Orsak | |
| 6,500,177 B1 | 12/2002 | Martinelli et al. | |
| 6,520,961 B1 | 2/2003 | Marsh | |
| 6,520,962 B1 | 2/2003 | Taylor et al. | |
| 6,530,925 B2 | 3/2003 | Boudard et al. | |
| 6,533,785 B1 | 3/2003 | Frigg et al. | |
| 6,537,275 B2 | 3/2003 | Venturini et al. | |
| 6,562,038 B1 | 5/2003 | Morrison | |
| 6,565,564 B2 | 5/2003 | Hoffman et al. | |
| 6,572,616 B2 | 6/2003 | Termaten | |
| 6,575,972 B1 | 6/2003 | Gordon | |
| 6,579,292 B2 | 6/2003 | Taylor | |
| 6,613,049 B2 | 9/2003 | Winquist et al. | |
| 6,616,664 B2 | 9/2003 | Walulik et al. | |
| 6,620,164 B2 | 9/2003 | Ueyama et al. | |
| 6,623,483 B1 | 9/2003 | Kazakov et al. | |
| 6,652,523 B1 | 11/2003 | Evrard et al. | |
| 6,652,524 B1 | 11/2003 | Weiner | |
| 6,663,631 B2 | 12/2003 | Kuntz | |
| 6,702,814 B2 | 3/2004 | Walulik et al. | |
| 6,709,433 B1 | 3/2004 | Schoenefeld | |
| 6,716,212 B1 | 4/2004 | Pickens | |
| 6,730,086 B2 | 5/2004 | Hehli et al. | |
| 6,736,775 B2 | 5/2004 | Phillips | |
| 6,746,448 B2 | 6/2004 | Weiner et al. | |
| 6,793,655 B2 | 9/2004 | Orsak | |
| 6,840,939 B2 | 1/2005 | Venturini et al. | |
| 6,860,883 B2 | 3/2005 | Janowski et al. | |
| 2002/0042613 A1 | 4/2002 | Mata | |
| 2002/0165543 A1 | 11/2002 | Winquist et al. | |
| 2003/0069580 A1 | 4/2003 | Langmaid et al. | |
| 2003/0114852 A1 | 6/2003 | Biedermann et al. | |
| 2003/0120273 A1 | 6/2003 | Cole | |
| 2003/0149429 A1 * | 8/2003 | Ferrante et al. | 606/59 |
| 2003/0149430 A1 | 8/2003 | Ferrante et al. | |
| 2003/0181911 A1 | 9/2003 | Venturini | |
| 2003/0187432 A1 | 10/2003 | Johnson et al. | |
| 2003/0191467 A1 | 10/2003 | Hoffmann-Clair et al. | |
| 2003/0191468 A1 | 10/2003 | Hoffman et al. | |
| 2003/0216734 A1 | 11/2003 | Mingozzi et al. | |
| 2003/0225405 A1 | 12/2003 | Weiner | |
| 2003/0225406 A1 | 12/2003 | Weiner | |
| 2004/0044344 A1 | 3/2004 | Winquist | |

(56) References Cited

U.S. PATENT DOCUMENTS

| | | | |
|---|---|---|---|
| 2004/0057789 A1 | 3/2004 | Vagn-Erik | |
| 2004/0059330 A1 | 3/2004 | Biedermann et al. | |
| 2004/0059331 A1 | 3/2004 | Mullaney | |
| 2004/0073212 A1 | 4/2004 | Kim et al. | |
| 2004/0097942 A1 | 5/2004 | Allen et al. | |
| 2004/0097944 A1 | 5/2004 | Koman et al. | |
| 2004/0116926 A1 | 6/2004 | Venturini et al. | |
| 2004/0133199 A1 | 7/2004 | Coati et al. | |
| 2004/0133200 A1 | 7/2004 | Ruch et al. | |
| 2004/0138659 A1* | 7/2004 | Austin et al. | 606/54 |
| 2004/0181221 A1 | 9/2004 | Huebner et al. | |
| 2004/0249375 A1 | 12/2004 | Agee et al. | |
| 2005/0015087 A1 | 1/2005 | Walulik et al. | |
| 2005/0043730 A1 | 2/2005 | Janowski et al. | |

FOREIGN PATENT DOCUMENTS

| | | |
|---|---|---|
| DE | 3531762 | 4/1986 |
| DE | 3527342 | 2/1987 |
| DE | 3614305 | 11/1987 |
| DE | 3822742 | 1/1989 |
| DE | 3805178 | 8/1989 |
| DE | 3842255 | 6/1990 |
| DE | 3936192 | 5/1991 |
| DE | 4118303 | 1/1992 |
| DE | 19753010 | 6/1999 |
| EP | 314021 | 5/1989 |
| EP | 350925 | 1/1990 |
| EP | 383419 | 8/1990 |
| EP | 604697 | 7/1994 |
| EP | 628289 | 12/1994 |
| EP | 707832 | 4/1996 |
| EP | 1 021 902 | 7/2000 |
| EP | 1 021 992 | 7/2000 |
| EP | 1016381 | 7/2000 |
| EP | 1312316 | 5/2003 |
| EP | 1374787 | 1/2004 |
| FR | 2616059 | 12/1988 |
| FR | 2674120 | 9/1992 |
| FR | 2693648 | 1/1994 |
| FR | 2705881 | 12/1994 |
| FR | 2805147 | 8/2001 |
| GB | 2033758 | 5/1980 |
| GB | 2038638 | 7/1980 |
| GB | 2076657 | 12/1981 |
| GB | 2258155 | 2/1993 |
| JP | 5245160 | 9/1993 |
| JP | 2002172119 | 6/2002 |
| JP | 2002306502 | 10/2002 |
| JP | 2004141403 | 5/2004 |
| JP | 2004167062 | 6/2004 |
| WO | WO 9011727 | 10/1990 |
| WO | WO 9111150 | 8/1991 |
| WO | WO 9111151 | 8/1991 |
| WO | WO 9202185 | 2/1992 |
| WO | WO 9207526 | 5/1992 |
| WO | WO 9412113 | 6/1994 |
| WO | WO 9423662 | 10/1994 |
| WO | WO 9510240 | 4/1995 |
| WO | WO 8606270 | 2/1996 |
| WO | WO 9612443 | 5/1996 |
| WO | WO 9730650 | 8/1997 |
| WO | WO 9832385 | 7/1998 |
| WO | 99/19988 | 4/1999 |
| WO | WO 9925265 | 5/1999 |
| WO | WO 02065927 | 8/2002 |
| WO | WO 02094112 | 11/2002 |
| WO | 2004/110289 | 12/2004 |
| WO | 2005/020829 | 3/2005 |

* cited by examiner

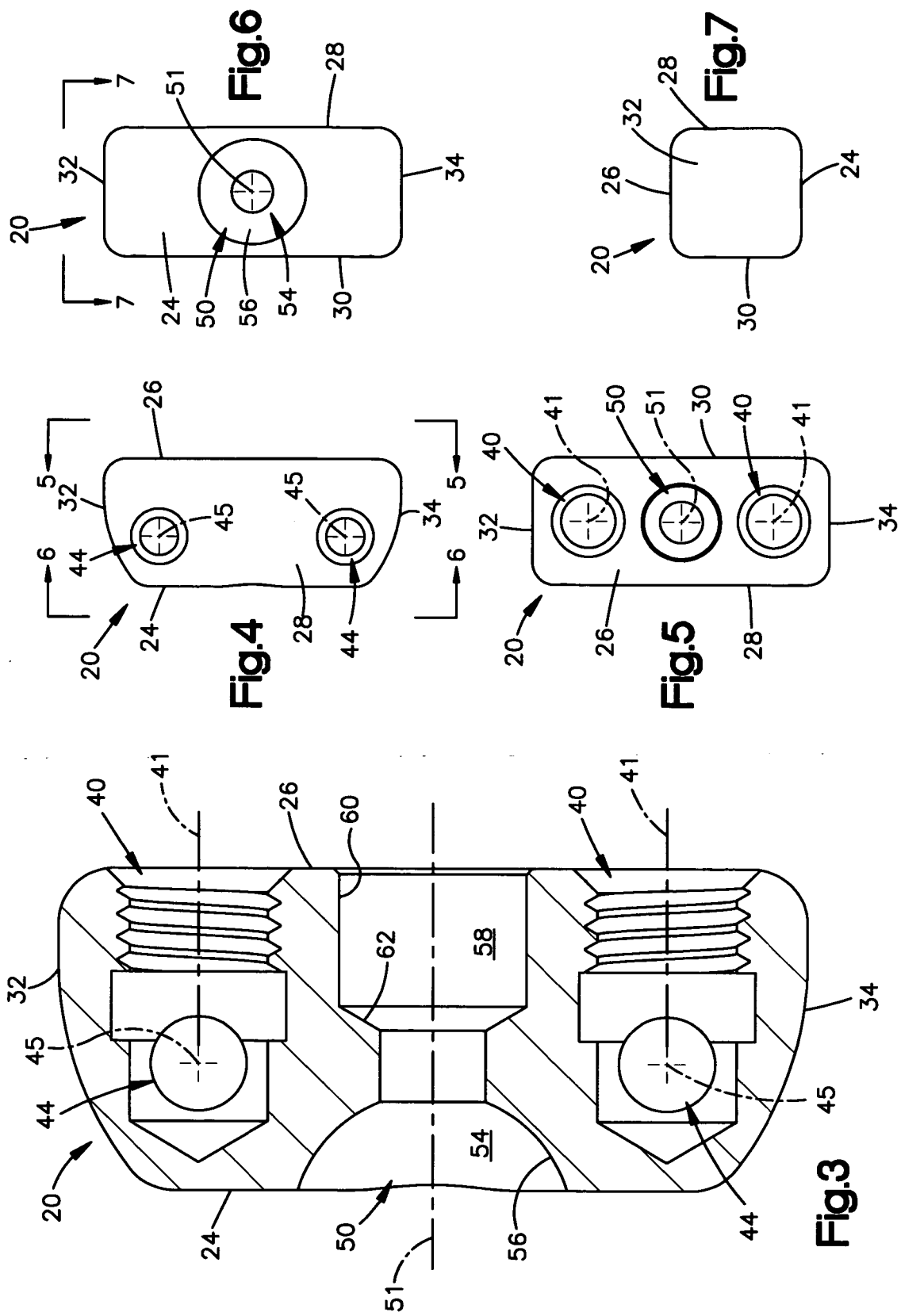

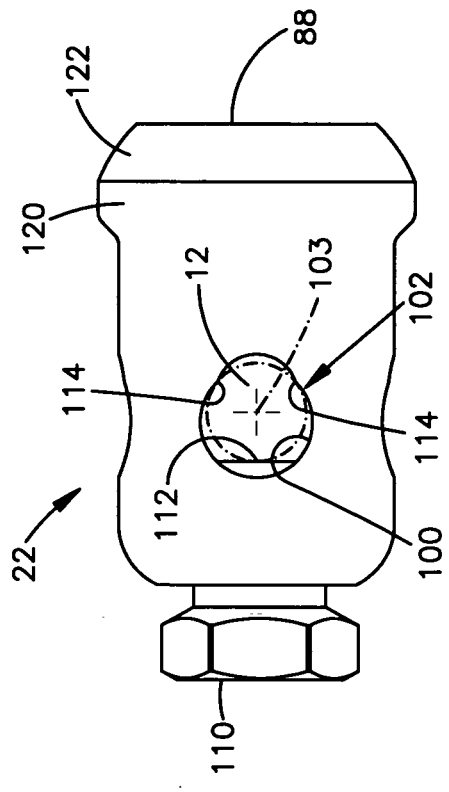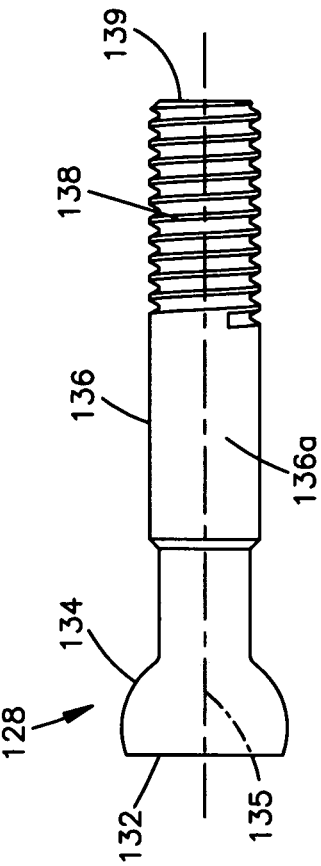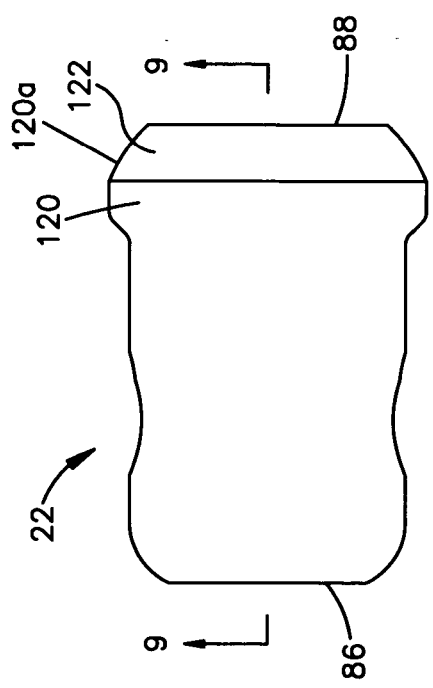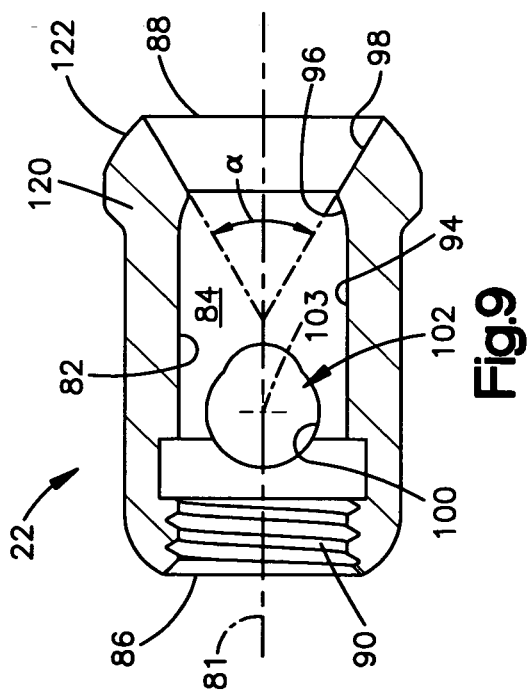

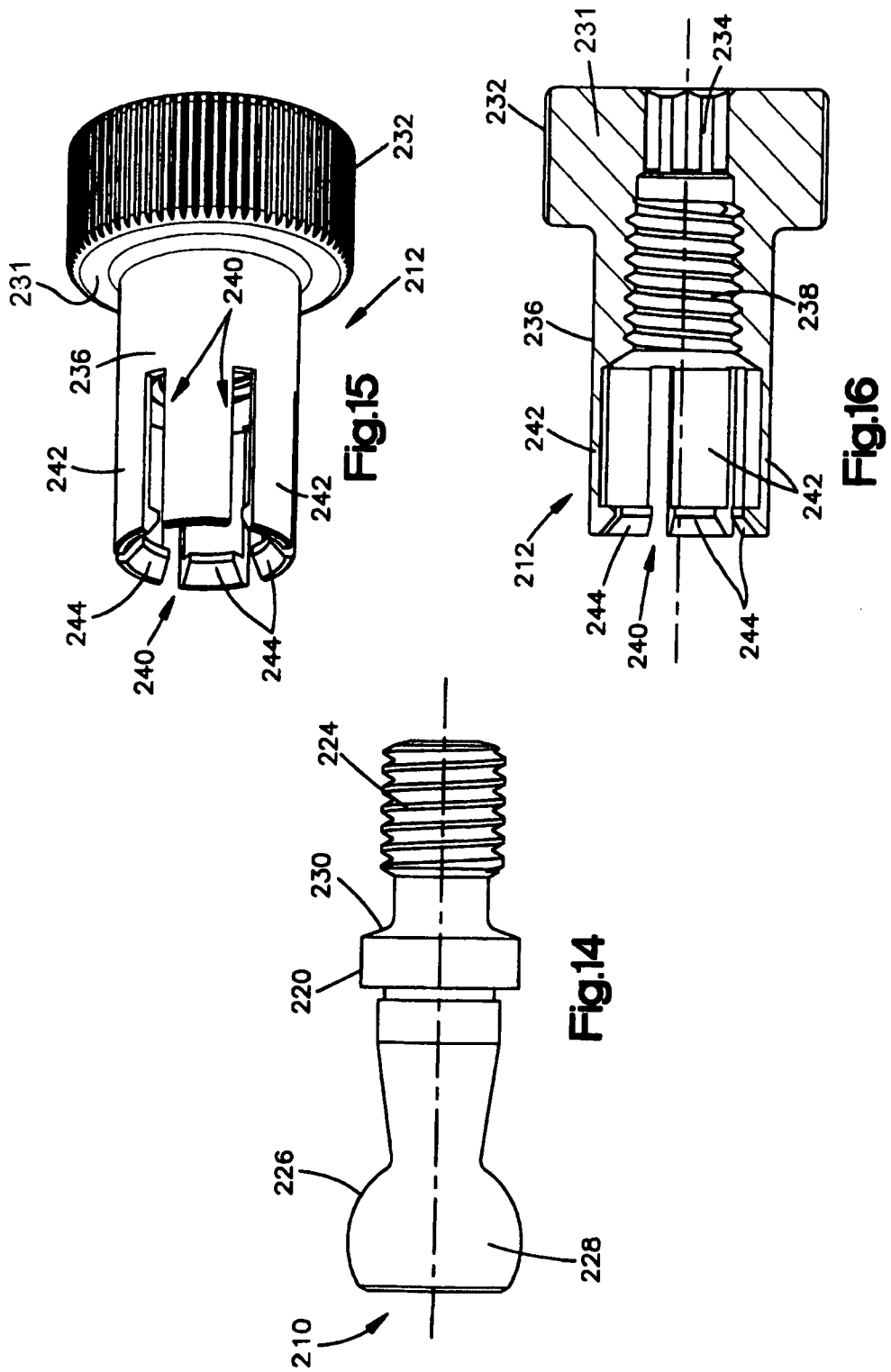

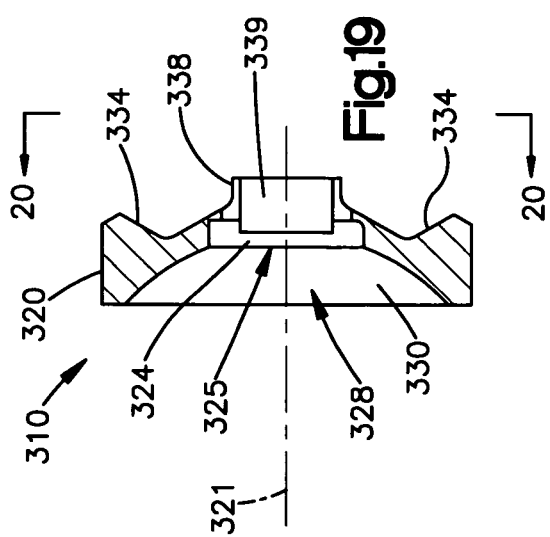
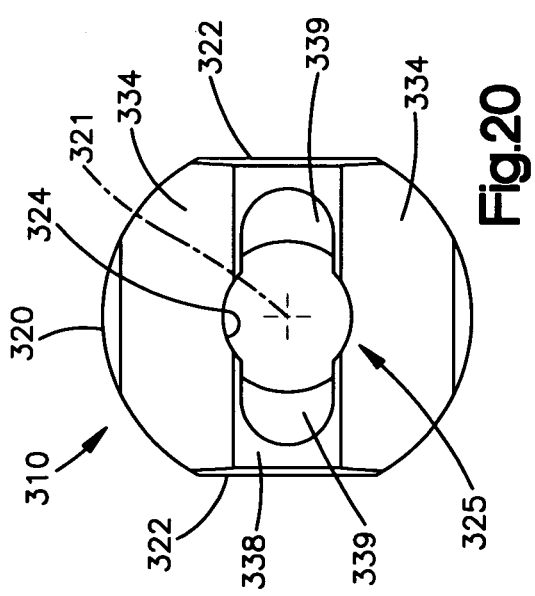
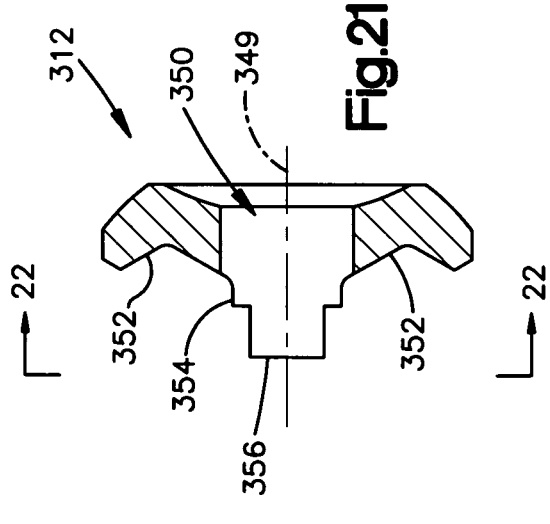
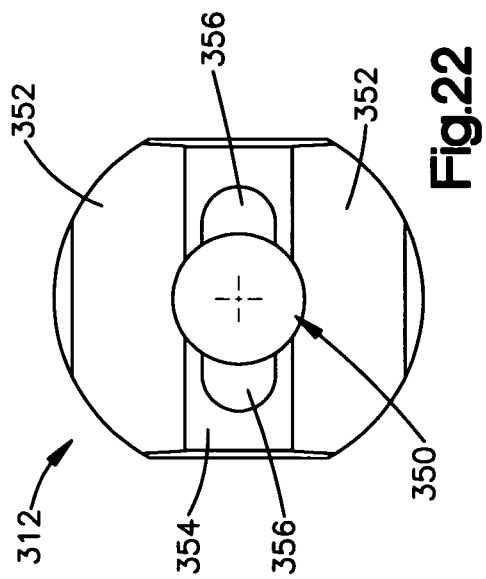

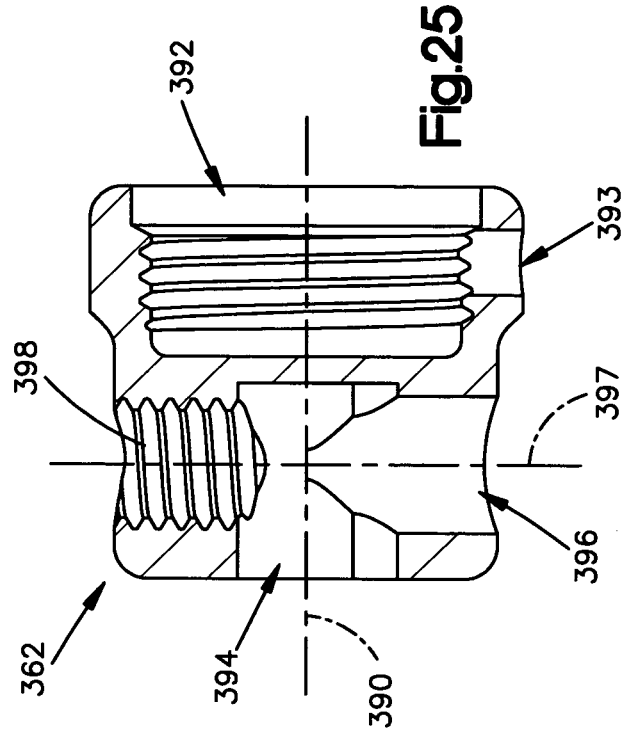
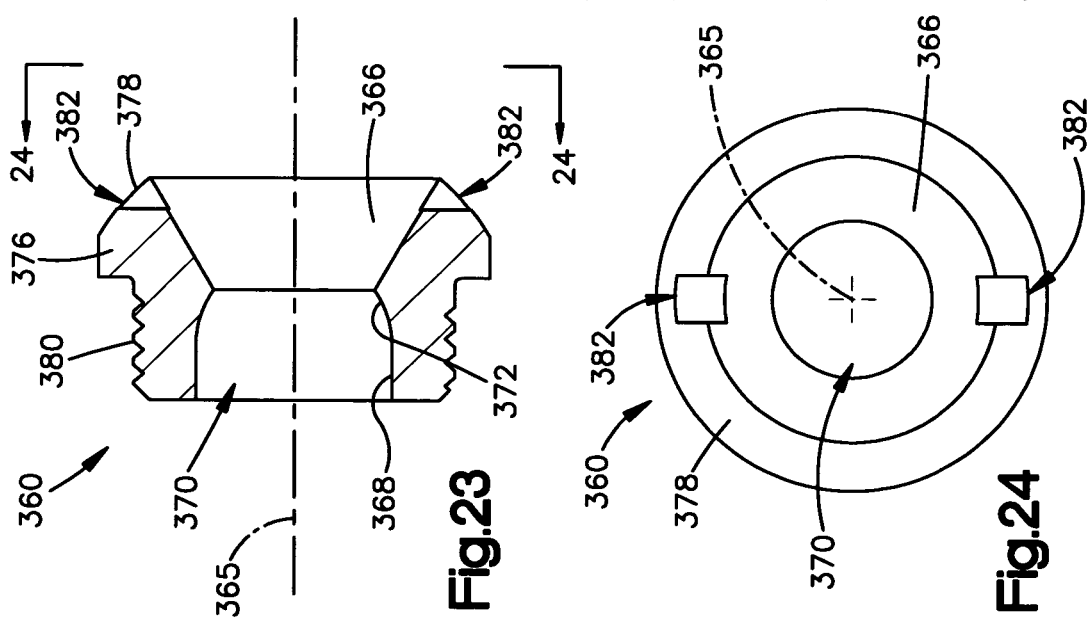

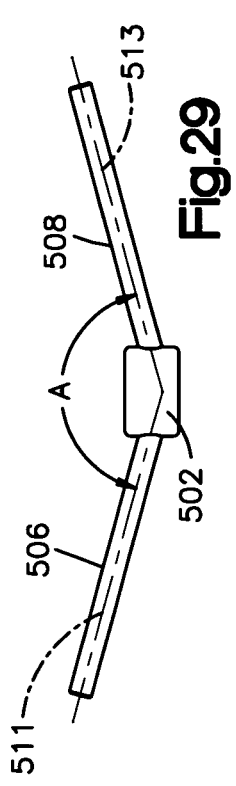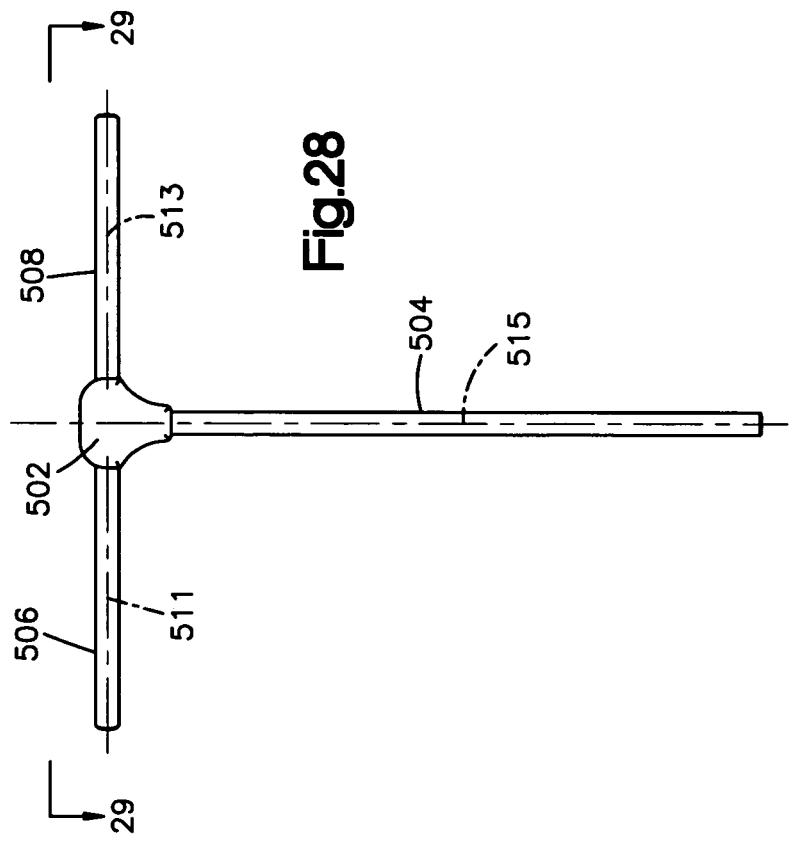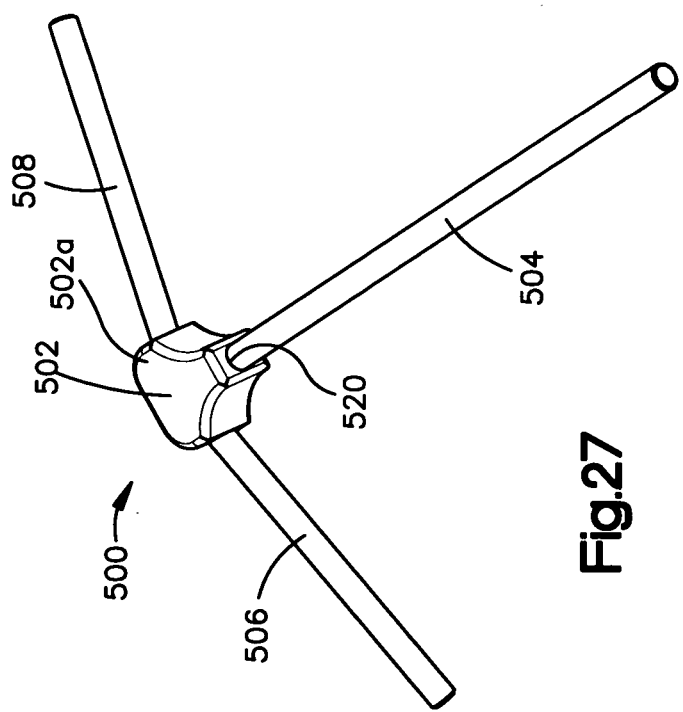

BONE FIXATION APPARATUS

TECHNICAL FIELD

The present invention relates to a bone fixation frame constructed by an orthopedic surgeon and, in particular, relates to an apparatus for engaging bone fixation elements in a bone fixation frame.

BACKGROUND

An orthopedic surgeon may construct a bone fixation frame to support bones on opposite sides of a fracture. The frame may include bone screws and pins that extend into or through the bones. The screws and pins may be clamped to bars that interconnect and retain them in their positions relative to each other. Some of the screws, pins and bars may be clamped together at right angles, but the configuration of the frame may require different angles that are established by the surgeon while constructing the frame. Accordingly, some bone fixation clamps are articulated to provide a range of angular positions for the interconnected parts of the frame.

SUMMARY

The claimed invention provides an apparatus for engaging bone fixation elements in a bone fixation frame. The apparatus may include first and second clamp structures which may be configured to engage first and second bone fixation elements, respectively. The first clamp structure may have a first spherically contoured bearing surface. The second clamp structure may have a second spherically contoured bearing surface which may be seated in sliding contact with the first bearing surface. Moreover, the apparatus may include a fastening element (e.g., bolt or connector) having a third spherically contoured bearing surface which may be seated in sliding contact with a fourth spherically contoured bearing surface in the second clamp structure. The apparatus may further include a spring-loaded mechanism that is operative to apply a spring force urging the bearing surfaces together to resist pivotal movement of the clamp structures relative to each other.

In one embodiment, a spring-loaded mechanism may be operative to vary the applied spring force. In another embodiment, the spring loaded mechanism may be operative in a first condition to apply only the spring force to urge the bearing surfaces together, and may be operative in a second condition to apply both the spring force and an additional force to urge the bearing surfaces together, thereby fixing the first and second clamp structures relative to each other. The spring force may be increased as the preferred mechanism is shifted from the first condition toward the second condition.

The invention also provides an assembly of bone fixation elements for use in a bone fixation frame. The assembly may include a plurality of bone fixation elements, and a connector device which may permanently interconnect the bone fixation elements immovably relative to each other.

BRIEF DESCRIPTION OF THE DRAWINGS

The present invention can be better understood by reference to the following drawings, wherein like references numerals represent like elements. The drawings are merely exemplary to illustrate certain features that may be used singularly or in combination with other features and the present invention should not be limited to the embodiments shown.

FIG. 3 is a separate view of a part shown in FIG. 2;
FIG. 4 is a side view of the part shown in FIG. 3;
FIG. 5 is a rear view taken on line 5-5 of FIG. 4;
FIG. 6 is a front view taken on line 6-6 of FIG. 4;
FIG. 7 is a top view taken on line 7-7 of FIG. 6;
FIG. 8 is a side view of a part shown in FIG. 2;
FIG. 9 is a sectional view taken on line 9-9 of FIG. 8;
FIG. 10 is a different side view of the part shown in FIG. 8, with other parts added;
FIG. 11 is a side view of another part shown in FIG. 2;
FIG. 14 is an enlarged side view of a part shown in FIG. 13;
FIG. 15 is an enlarged perspective view of a part shown in FIG. 13;
FIG. 16 is a sectional view of the part shown in FIG. 15;
FIG. 19 is a separate view of a part shown in FIG. 18;
FIG. 20 is a view taken on line 20-20 of FIG. 19;
FIG. 21 is a separate view of a part shown in FIG. 18;
FIG. 22 is a view taken on line 22-22 of FIG. 21;
FIG. 23 is a separate view of another part shown in FIG. 18;
FIG. 24 is a view taken on line 24-24 of FIG. 23;
FIG. 25 also is a separate view of a part shown in FIG. 18;
FIG. 27 is a perspective view of an assembly of bone fixation elements;
FIG. 28 is a top view of the assembly of FIG. 27;
FIG. 29 is an end-view taken on line 29-29 of FIG. 28.

DETAILED DESCRIPTION

Figure 1:
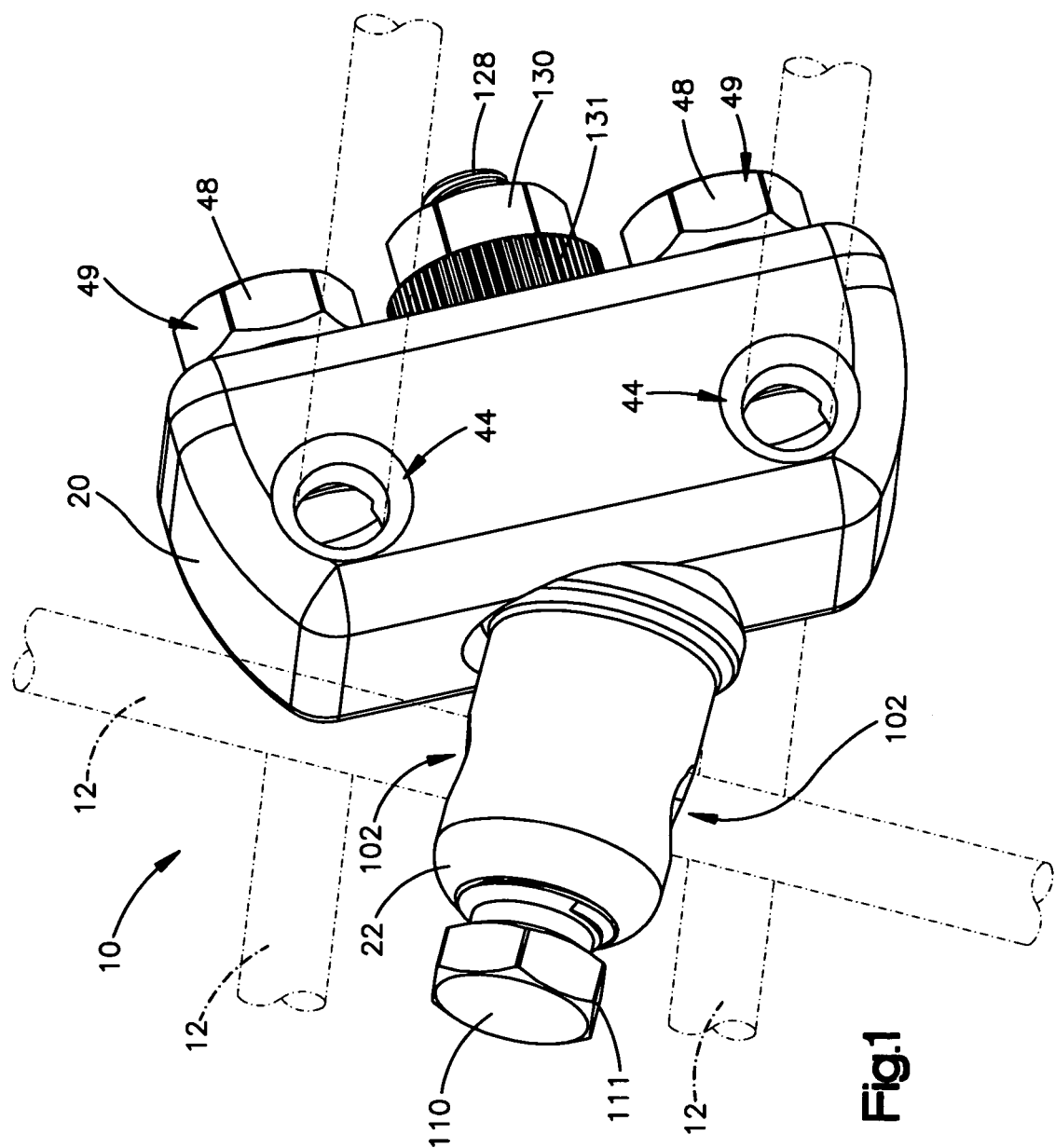
FIG. 1 is a perspective view of a clamp assembly with associated bone fixation elements.

The device 10 shown in FIG. 1 is an articulated clamp assembly for supporting bone fixation elements 12 (shown in phantom lines in FIG. 1) in a bone fixation frame. Such a frame may be used to fix bone fragments relative to each other, including, for example, in the wrist, hand, feet, jaw, vertebrae, ribs, arm, leg and/or long bones. The fixation elements 12 (shown partially) may be known items such as, for example, bone screws, bone pins, bone wires, bars, rods and/or rings. The clamp assembly 10 may be used by a surgeon to assemble a bone fixation frame by interconnecting the fixation elements 12. Articulation of the clamp assembly 10 may provide a wide range of angular configurations in which the fixation elements 12 may be interconnected in the frame.

Figure 2:
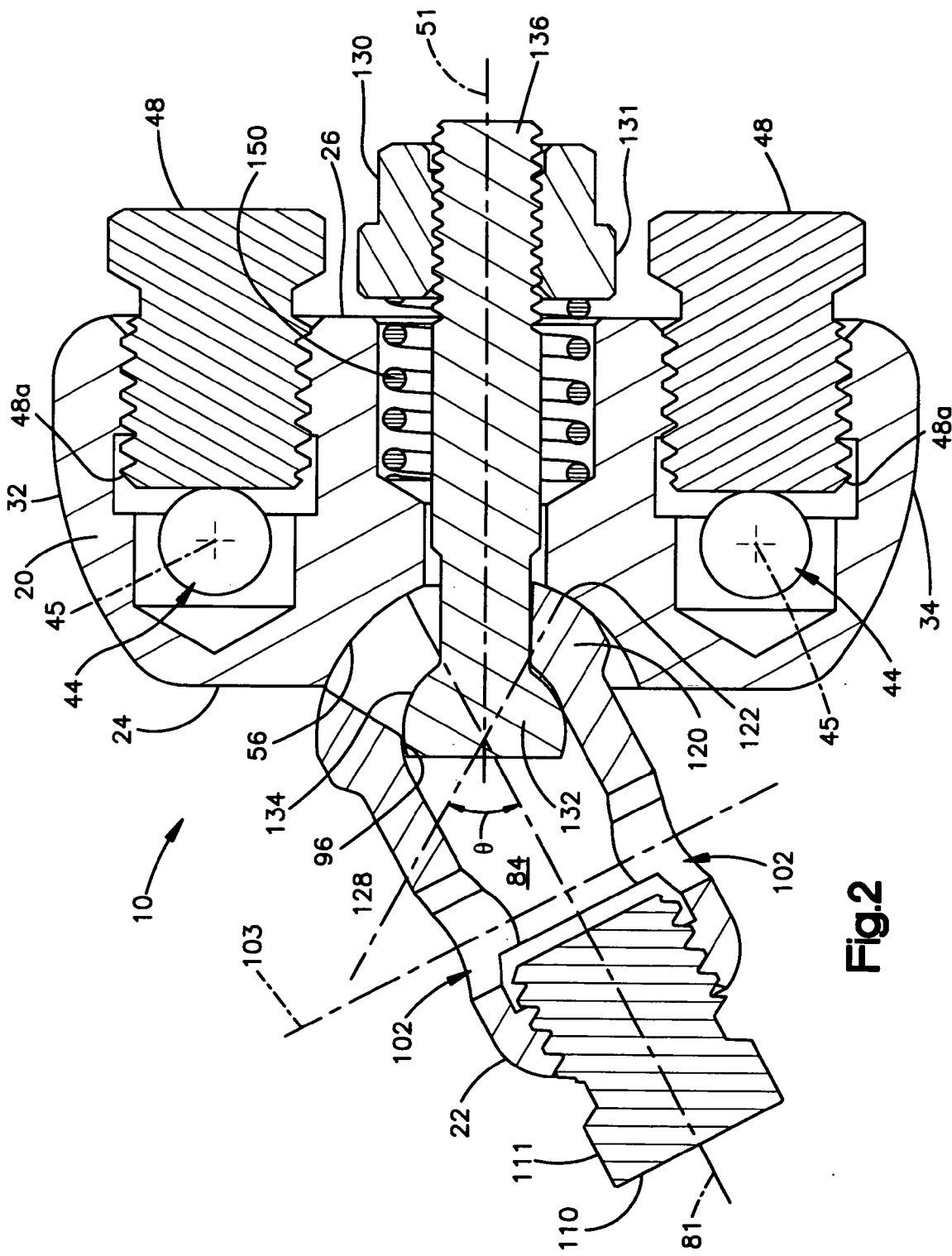
FIG. 2 is an enlarged sectional view of the clamp assembly of FIG. 1.

As shown in FIGS. 1 and 2, the clamp assembly 10 may include first and second clamp structures 20 and 22 which may engage the fixation elements 12. It should, however, be understood that those of ordinary skill in the art will recognize many modifications and substitutions which may be made to various elements of the present invention.

The clamp structures 20 and 22 may be sized for use, for example, in a wrist fixation frame, and each clamp structure 20 and 22 may be a unitary part, which may consist of, for example, a single body of cast metal material or bar stock that may be machined or forged into shape. Alternatively, the clamp structures 20 and 22 may be made of two or more pieces joined together, for example, by welding, adhesive, press fitting, soldering or by using pins, threads or some combination thereof. As shown separately in FIGS. 3-7, the first clamp structure 20 may be a generally rectangular body with a generally planar front surface 24, a generally planar rear surface 26, and a pair of generally planar opposite side surfaces 28 and 30. The rectangular shape may be rounded at the peripheral corners and edges, and may be tapered where opposite end surfaces 32 and 34 converge toward the front side surface 24. It should be appreciated, however, that any other shape may be used (e.g., square, other polygon, or complex or irregular shape).

As shown in FIG. 5, a pair of screw-threaded counterbores 40 may extend into the first clamp structure 20. The counterbores 40 may be similar or identical in structure to each other and may each extend inward from the rear surface 26 along a respective axis 41. The axes 41 of the counterbores 40 may be parallel, perpendicular or at an oblique angle relative to each other. A pair of bores 44 may extend through the first clamp structure 20 between the opposite side surfaces 28 and 30. The bores 44 may be similar or identical in structure to each other. Each bore 44 may be centered on an axis 45 that intersects, and may be at an angle (e.g., perpendicular) to, the axis 41 of a corresponding counterbore 40 so that each of bores 44 may intersect and communicate with the counterbores 40. The axes 45 of the bores 44 may be parallel, perpendicular or at an oblique angle relative to each other. Moreover, each bore 44 may be configured to receive a bone fixation element 12 which may extend through the first clamp structure 20 along the axis 45. The bores 44 may be any shape, including circular, oval, square, rectangular or other polygon. Those skilled in the art will appreciate that any shape may be used so long as the bores 44 may receive a fixation element 12. In an embodiment where the bores 44 may be circular in shape, the bores 44 may have a diameter, for example, between about 1 mm and about 8 mm, more preferably between about 1.25 mm and about 6.5 mm and, most preferably, between about 3.5 mm and about 5.5 mm. Each bore 44 may also be configured such that a fixation element 12 may be held securely in place (e.g., may be prevented from moving in an axial direction along the axes 45) by one of a pair of set screws 48 (FIGS. 1 and 2) installed in the counterbores 40. The screw threads on the set screws 48 may preferably be deformed at their inner ends 48a to prevent removal of the set screws 48 from the clamp structures 20. Such deformation may be accomplished by screwing set screws 48 into counterbores 40 until the inner ends 48a of the screws 48 are accessable through bores 44. A tool may be inserted through the bores 44 and may be used to deform the inner ends 48a of the screws 48 to prevent the screws 48 from being removed from counterbores 40. Other methods of retaining the screws 48 coupled to the clamp structure 20 may be used. Moreover, the set screws 48 may have an engagement surface 49 which may be used to loosen and/or tighten the set screws 48 in the counterbores 40 (e.g., a surgeon may grasp the engagement surface 49 with his/her fingers and/or a tool to rotate the set screws 48). For example, the engagement surface 49 may take the form of a hexagon having surfaces for engagement with a tool. It should be noted, however, than any structure or mechanism that may hold a fixation element 12 to the first clamp structure 20, or within the bores 44 is envisioned.

The first clamp structure 20 may further have a central bore 50. The central bore 50 may extend between the front and rear surfaces 24 and 26, and may have a central axis 51 which may be parallel to or at an angle with the axes 41 of the counterbores 40. A socket portion 54 of the central bore 50 may be defined by a bearing surface 56 which may be recessed from the front surface 24 with a concave spherical contour centered on or offset from the axis 51. A rear portion 58 of the central bore 50 may be defined in part by a cylindrical surface 60 which may extend axially inward from the rear surface 26, and in part by an annular shoulder surface 62 at the inner end of the cylindrical surface 60.

As shown separately in FIGS. 8 and 9, the second clamp structure 22 may be a generally elongated tubular body with a longitudinal central axis 81. An inner surface 82 may define a passage 84 extending axially through the second clamp structure 22 between its opposite ends 86 and 88. A first end portion 90 of the inner surface 82 may define a screw thread extending axially inward from the first end 86. A major portion 94 of the inner surface 82 may be cylindrical. An adjacent portion 96 of inner surface 82 may be tapered radially inward from the cylindrical major portion 94 toward the second end 88. The adjacent portion 96 may be configured as a bearing surface with a concave spherical contour which may be centered on or offset from the axis 81. It should be noted, however, that the adjacent portion 96 may be configured in shapes other than concave so long as adjacent portion 96 may engage the bearing surface (e.g., surface 134) of a connector (e.g., bolt 128). A second end portion 98 of the inner surface 82 may have a conical contour extending axially and radially outward from the adjacent portion 96 to the second end 88.

The second clamp structure 22 may have a pair of inner surfaces 100 which may define a respective pair of apertures 102. In one embodiment, the apertures 102 may be connected such that the apertures 102 may form part of a channel passing through the second clamp structure 22. The apertures 102 may be spaced a distance from the threaded first end portion 90, and may be centered on an axis 103, which may be at an angle (e.g., perpendicular) with respect to the longitudinal axis 81. The apertures 102 may communicate with and intersect the passage 84. Such a configuration may provide a passage through which the fixation element 12 of FIG. 1 may extend through the second clamp structure 22. The apertures 102 may be sized to receive a fixation element 12 which may have a dimension, for example, between about 1 mm and about 20 mm, more preferably between about 2.5 mm and about 11.5 mm and, most preferably, between about 3.5 mm and about 6.5 mm.

A set screw 110 (FIGS. 1 and 2) may be received in the longitudinal passage 84 to hold a fixation element 12 securely in the apertures 102. In an embodiment where the fixation element 12 has a smaller dimension than the apertures 102, for example, as shown in FIG. 10, the end surface 112 of the set screw 110 may press the fixation element 12 against a surface (e.g., corner portions 114) of each inner surface 100 of the apertures 102. Such a construction may provide clamping contact with the fixation element 12 at a plurality of locations which may be spaced-apart circumferentially about the axis 103. For example, as shown in FIG. 10, the apertures 102 may be sized and configured such that a fixation element 12 may have three points of contact—against two corner portions 114 and the end surface 112 of the set screw 110. The screw threads on the set screw 110 may preferably be deformed at their inner ends to prevent removal of the set screw 110 from the clamp structures 22. Moreover, the set screw 110 may have an engagement surface 111 which may be used to loosen and/or tighten the set screw 110 in the first end portion 90 (e.g., a surgeon may grasp the engagement surface 111 with his/her fingers and/or a tool to rotate the set screw 110).

As further shown in FIGS. 8 and 9, the second clamp structure 22 may have a radially enlarged base portion 120 at its second end 88. The outer surface 120a of the base portion 120 of the second clamp structure 22 may be configured as a spherical or ball end for pivotal movement in the socket 54 (FIG. 3) in the first clamp structure 20. In this manner, the structures 20 and 22 may be configured as a ball and socket joint that can undergo three dimensional articulated movement and even rotate about axes 51, 81. A bearing surface 122 of the base portion 120 may be tapered radially outward from the conical inner surface portion 98, and may have a convex spherical contour centered on the longitudinal axis 81. That bearing surface 122 may be seated in sliding contact with the bearing surface 56 in the socket 54, as shown in FIG. 2. The first and second clamp structures 20 and 22 may have a range of motion θ (FIG. 2) relative to each other, for example, between about 0 degrees and about 90 degrees, more preferably, between about 30 degrees and about 70 degrees and, most preferably, between about 45 degrees and about 65 degrees. The range of motion θ may be related to the angle α of the conical inner surface portion 98 which may be, for example, between about 30 degrees and about 90 degrees, more preferably, between about 40 degrees and about 80 degrees and, most preferably, between about 50 degrees and about 70 degrees. It should be noted that any other embodiments of the present invention may have the same range of motion θ as the embodiment of FIG. 2. Moreover, the concave and/or convex bearing surfaces 56, 122 may have a radius of curvature, for example, between about 2 mm and about 15 mm, more preferably about 5 mm and about 10 mm and, most preferably, between about 5.5 mm and about 9 mm. The radius of curvature of bearing surfaces 56 and 122 may be different or the same. In a preferred embodiment, however, the radius of curvature of bearing surface 122 may be equal to or greater than the radius of curvature of bearing surface 56. Convex or concave surfaces in any embodiment of the present invention may have the same radius of curvature as the surfaces 56, 122.

The concave bearing surface 56 may not extend circumferentially about the convex bearing surface 122 sufficiently to capture the base portion 120 of the second clamp structure 22 in the socket 54. Instead, the base portion 120 of the second clamp structure 22 may be held in the socket 54 by a connector device such as bolt 128 (FIG. 11) and a tightening device 130 (FIG. 2). In one embodiment, the tightening device 130 may be a nut with a splined peripheral gripping surface 131. The connector device may be a bolt 128 which may have a head 132 with a convex spherical bearing surface 134 centered on a longitudinal central axis 135. The bolt 128 may also have a stem 136 with a screw thread 138 which may extend axially from the end 139 toward the head 132. The bolt 128 may also have an unthreaded shank portion 136a.

As shown in FIG. 2, the head 132 of the bolt 128 may be received in the passage 84 in the second clamp structure 22 such that bearing surface 134 on the head 132 may be seated in sliding contact with the bearing surface 96 in the passage 84. In a preferred embodiment, the radius of curvature of the bearing surfaces 96, 134 may be less than the radius of curvature of the bearing surface 122, and the bearing surface 96 may be concentric with the bearing surface 122. Moreover, bearing surface 134 may be substantially concentric with bearing surface 122. The stem 136 on the bolt 128 may project through the adjacent open end of the passage 84, and may extend through the central bore 50 in the first clamp structure 20 so that the axis 51 of the bore 50 may be aligned with the axis 135 of the bolt 128 (i.e., coaxial). The nut 130 may be screwed onto the stem 136 at the rear of the first clamp structure 20. In one preferred embodiment, the screw thread 138 on the bolt 128 may be deformed at its outer end 139 to prevent removal of the nut 130 from the bolt 128. Other methods of retaining the nut 130 on the bolt 128 may also be used.

A spring 150 may be received in the rear portion 58 of the central bore 50 in the first clamp structure 20. The spring 150 may be compressed axially between the nut 130 and the inner shoulder surface 62. In this arrangement, the spring 150 may apply a force axially against the nut 130. The bolt 128 may transmit the axially directed spring force to the second clamp structure 22 to hold the two pairs of adjoining bearing surfaces 96, 134 and 56, 122 together and to resist pivotal movement of the two clamp structures 20 and 22 relative to each other. The spring force may be great enough to hold the clamp structures 20 and 22 from pivoting under the force of gravity. The spring force may also hold the bolt head 132 and the clamp structures 20 and 22 together tightly enough to restrain rotation of the bolt 128 so that the nut 130 may be rotated relative to the bolt 128 without the need for a key structure that blocks rotation of the bolt 128.

A surgeon may decrease the spring force applied to the components of the clamp assembly 10 by rotating the nut 130 along the bolt 128 in a first direction from the position shown in FIG. 2 (i.e., rearwardly or away from the first clamp structure 20). The surgeon may increase the spring force applied to the components of the clamp assembly 10 by rotating the nut 130 in a second direction, oppositely the first direction, to advance the nut 130 toward the first clamp structure 20. When the nut 130 is disengaged from the first clamp structure 20, a surgeon may pivot the clamp structures 20 and 22 into a variety of provisional positions relative to each other while, at the same time, keeping the clamp structures 20 and 22 in contact with each other and under the influence of the spring force. Such a construction may allow for the concave bearing surface 56 and the convex bearing surface 122 to slide with respect to each other and for the first and second clamp structures 20 and 22 to be held in a variety of positions before tightening the nut 130. A tightening force may then be added to the spring force by tightening the nut 130 against the rear surface 26. Upon tightening the nut 130 to the first clamp structure 20, the clamp structures 20 and 22 may be fixed with respect to each other.

Figure 12:
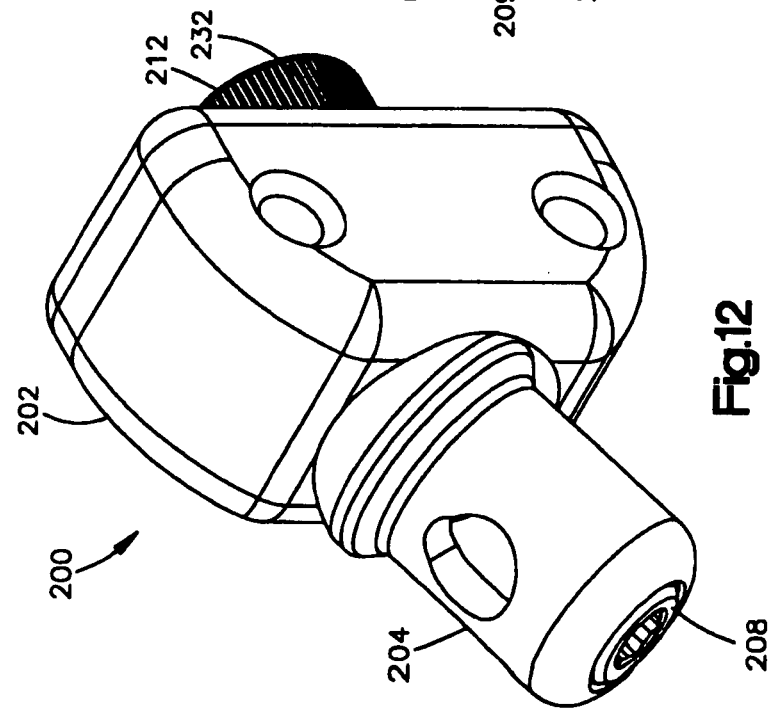
FIG. 12 is a perspective view of another clamp assembly for bone fixation elements.

The device 200 shown in FIG. 12 is an articulated clamp assembly similar to the clamp assembly 10 described above. Similar to the clamp assembly 10, clamp assembly 200 may include first and second clamp structures 202 and 204. The clamp structures 202 and 204 may be interconnected for articulated or pivotal movement relative to each other in the same manner as the clamp structures 20 and 22, and may be likewise configured to engage fixation elements 12.

Figure 13:
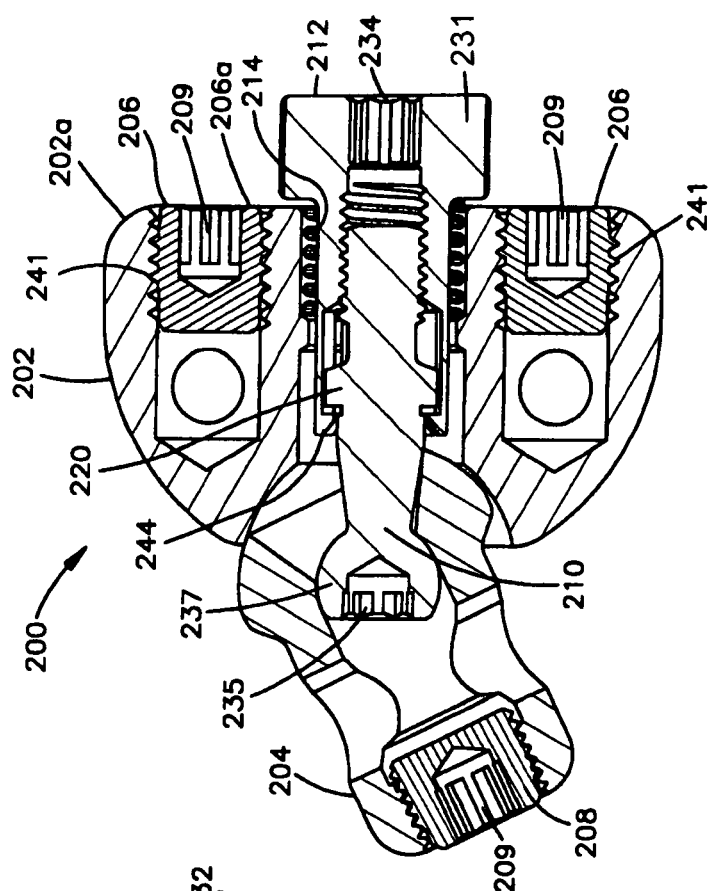
FIG. 13 is a sectional view of the clamp assembly shown in FIG. 12.

As shown in FIG. 13, the clamp assembly 200 may include set screws 206 and 208 with recesses 209 for engagement by a tool (e.g., wrench). The recesses 209 may be configured as a hexagon or other shape for receiving a tool which can apply a torque to the set screws 206, 208. It should be noted that the screws 206 may be inserted into the counterbores 241 such that the surface 206a of the screws 206 may be positioned below the surface 202a. A tool may be used to deform the threads of the counterbores 241 proximate the surface 202a, thereby preventing the screws 206 from being removed from the counterbores 241. Although the clamp assembly 200 may include a connector device 210, a tightening device 212 and a spring 214 for applying variable spring forces as described above, the connector device 210 and the tightening device 212 in the clamp assembly 200 may be structurally and functionally different from their counterparts in the clamp assembly 10.

As shown in FIG. 14, the connector device 210 may be a bolt with a flange 220 located between a screw thread 224 and a bearing surface 226 on a head 228. A cam surface 230 may be located at one side of the flange 220. Moreover, as shown in FIGS. 15 and 16, the tightening device 212 may be an internally threaded knob. The tightening device 212 may have a cylindrical head 231 with a gripping surface 232 which may have, for example, ridges. Recess 234 may be located within the head 231 and may receive a tool to rotate the tightening device 212. The recess 234 may be configured as a hexagon or other shape for receiving a tool which can apply a torque to the tightening device 212. A recess 235 may also be located at the end 237 of the connector device 210 and may receive a tool, for example, to hold the connector 210 in place (i.e., provide resistance) as the tightening device 212 is screwed onto the connector 210 and towards the first clamp structure 202. A stem portion 236 of the tightening device 212 may project from the head 231. Furthermore, an internal screw thread 238 may be positioned within the tightening device 212 and, in one embodiment, may be located partially within the head 231 and partially within the stem 236.

The stem 236 may have a plurality of axially extending slots 240 which may be located between a corresponding array of axially extending arms 242. Each arm 242 of the stem 236 may have a wedge-shaped locking tab 244 projecting radially inward. The arms 242 may be flexible so that the tabs 244 may move radially outward when pushed against the cam surface 230 and may snap back inward behind the flange 220 as the tightening device 212 is screwed onto the bolt 210. The engagement of the tabs 244 and the flange 220 may prevent disengagement of the tightening device 212 from the bolt 210. Such a construction may enable the first and second clamp structures 202 and 204 to move (e.g., slide) with respect to each other while, at the same time, keeping the structures 202 and 204 attached to each other and provisionally held in a variety of orientations relative to each other. Upon tightening the tightening device 212 (i.e., moving the tightening device 212 towards the first clamp structure 202), the first and second clamp structures 202 and 204 may be held more firmly against each other until the clamp structures 202 and 204 may be rigidly fixed in a particular orientation with respect to each other.

Figure 17:
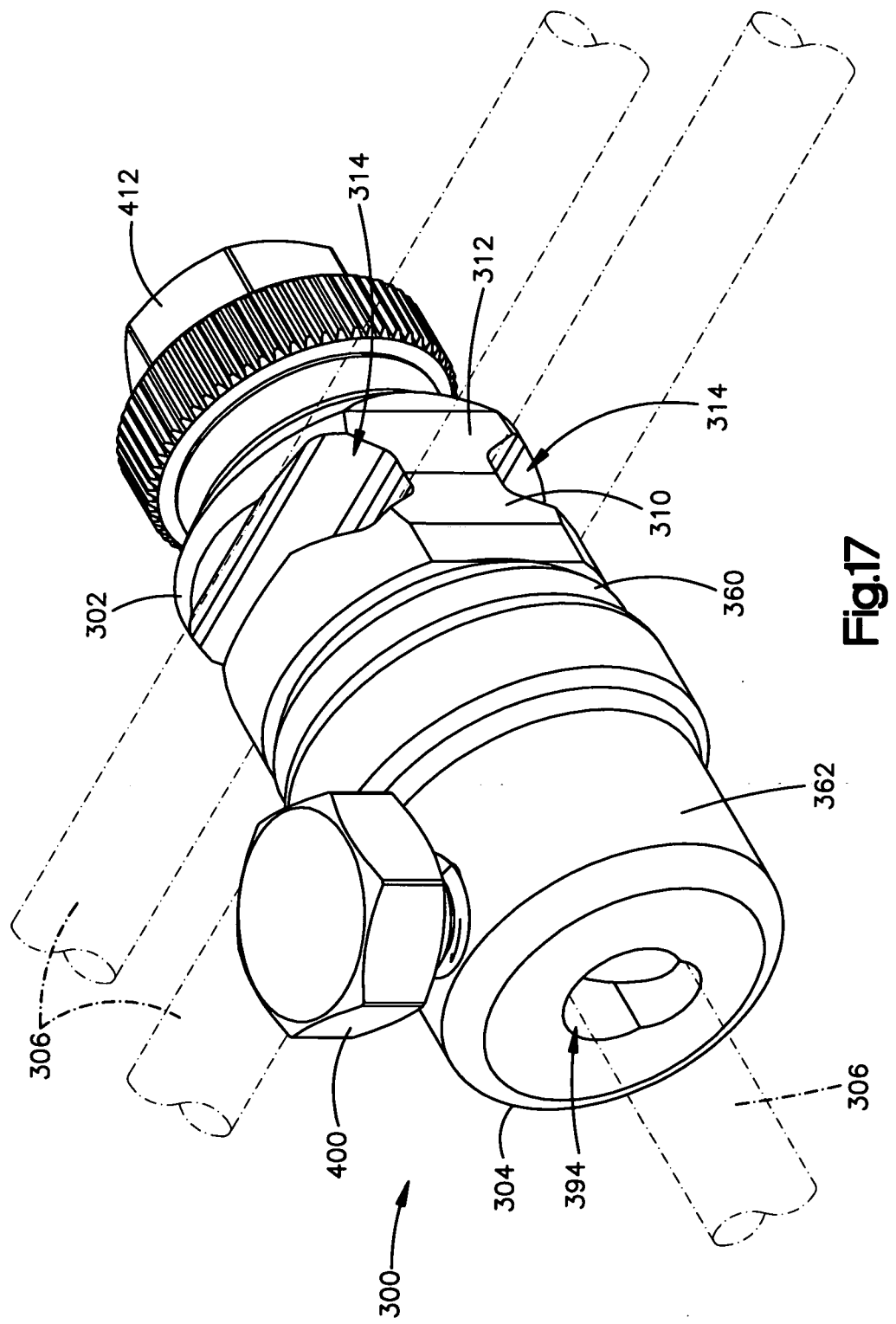
FIG. 17 is a perspective view of yet another clamp assembly for bone fixation elements.

Yet another embodiment of the present invention is shown in FIG. 17. Clamp assembly 300 may include first and second clamp structures 302 and 304 for engaging fixation elements 306 (shown in phantom in FIG. 17). Clamp assembly 300 may be articulated so that the clamp structures 302 and 304 may be articulated, pivotally moved or twisted relative to each other against the variable resistance of a spring-loaded mechanism within the clamp assembly 300.

Figure 18:
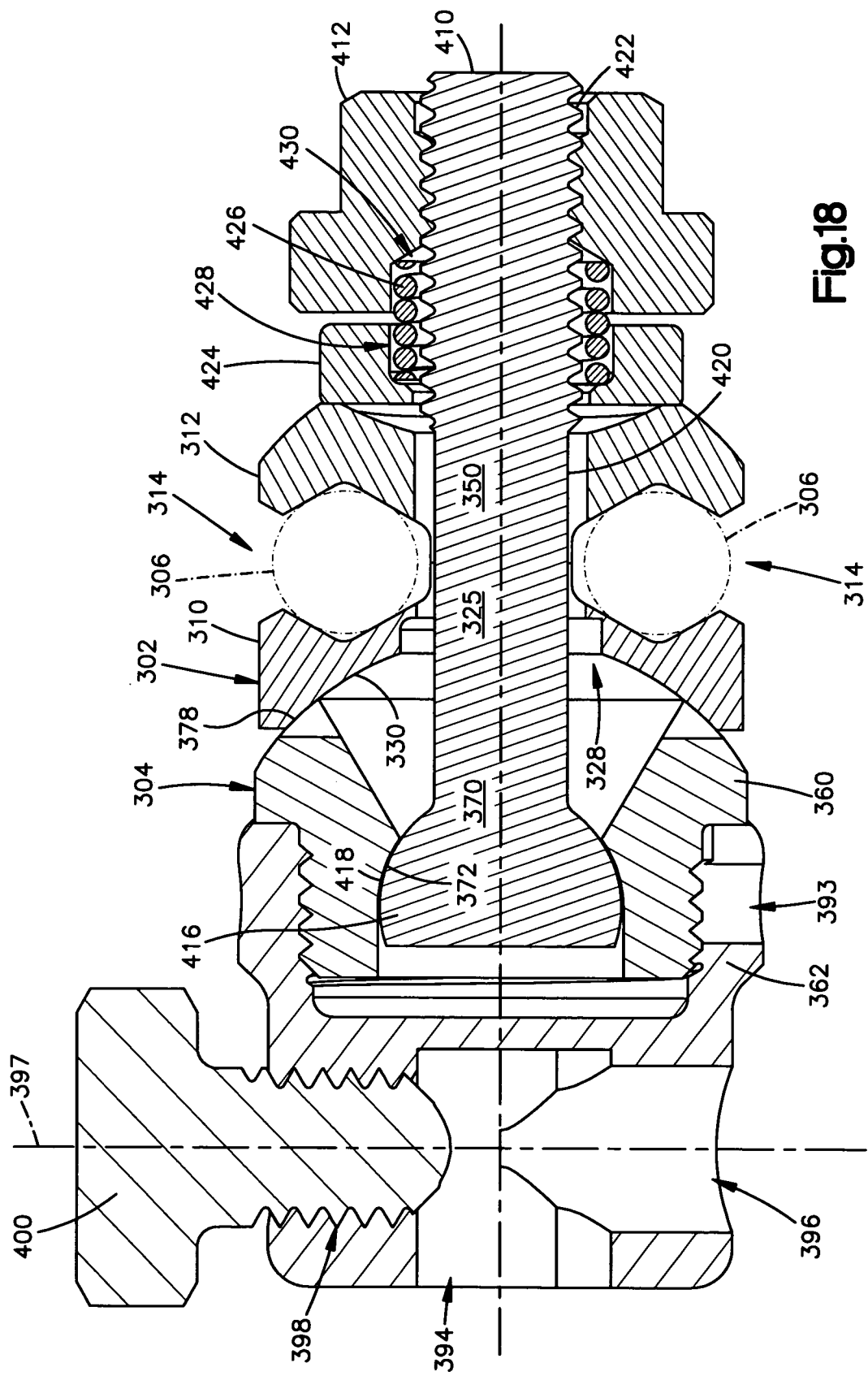
FIG. 18 is a sectional view of the clamp assembly of FIG. 17.

As shown in FIGS. 17 and 18, two opposed pieces 310 and 312 of the first clamp structure 302 may define a pair of channels 314 for receiving a pair of the fixation elements 306. As shown in FIGS. 19 and 20, the first piece 310 may be shaped generally as a plate with a circular peripheral surface 320 centered on an axis 321. The circular surface 320 may be interrupted by a pair of diametrically opposed flat surfaces 322. An annular inner surface 324 may define a circular opening 325, which may be centered on the axis 321.

A socket 328 in the first piece 310 may be defined by a recessed surface 330 with a concave spherical contour, which may be centered on or offset from the axis 321. The first piece 310 may also have a pair of recessed surfaces 334 with contours (e.g., angular contours). The recessed surfaces 334 may define trough-shaped side walls of the two channels 314. A mid-section 338 of the first piece 310 may extend diametrically across the first piece 310. The mid-section 338 may have one or more pockets 339 on opposite sides of the central opening 325.

The second piece 312 (FIGS. 21 and 22) may also be shaped as a generally circular plate with a central axis 349, a circular central opening 350, and a pair of recessed rear surfaces 352, which may define trough-shaped side walls of the two channels 314. A mid-section 354 at the rear of the second piece 312 may have one or more axial projections 356 that fit closely within the pockets 339 on first piece 310 such that the two pieces 310 and 312 may fit coaxially together. Such a construction may prevent the pieces 310 and 312 from rotating with respect to each other about the axes 321 and 349.

Figure 21A:
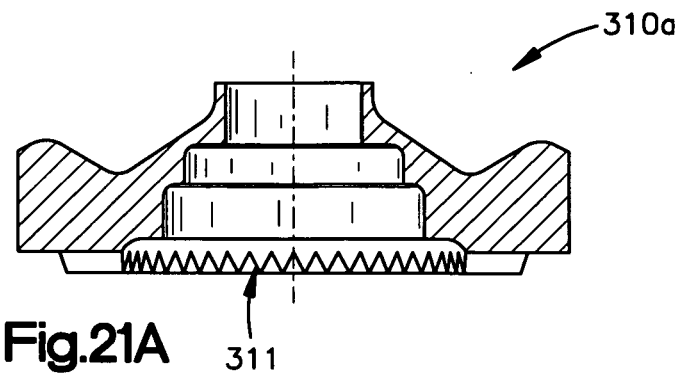
FIG. 21A is a separate view of a part for use in an alternative embodiment of the clamp of FIG. 18.
Figure 21B:
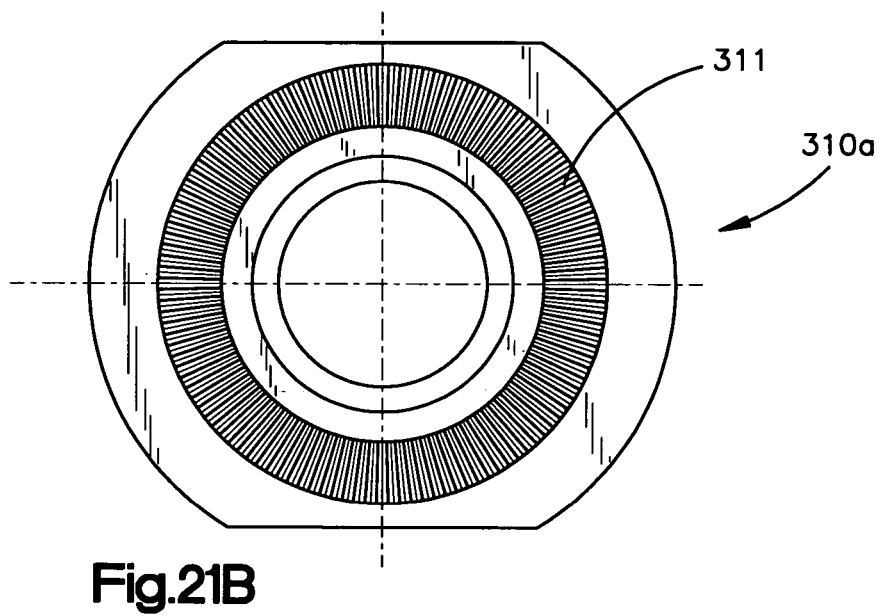
FIG. 21B is a bottom view of the part shown in FIG. 21A.
Figure 21C:
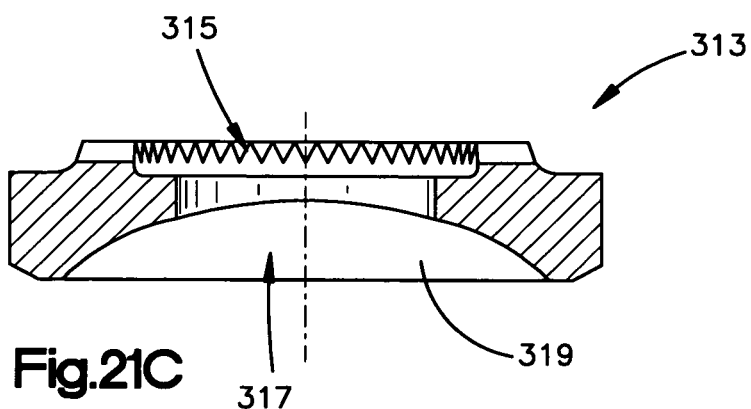
FIG. 21C is a separate view of a part for use in an alternative embodiment of the clamp of FIG. 18.

In another embodiment, the first clamp structure 302 may comprise an alternative first piece 310a (FIGS. 21A and 21B), the second piece 312, and a third piece 313 (FIG. 21C) which may be positioned between the first piece 310a and a second clamp structure 304. The first piece 310a may have a similar construction to the first piece 310, except the first piece 310a may have an engagement portion 311 and may alternatively or in addition have no socket. As shown in FIGS. 21A and 21B, the engagement portion 311 may be serrated. The engagement portion 311 may engage a corresponding engagement portion 315 (e.g., serrations) on the third piece 313. A spring (not shown) may be positioned between the first piece 310a and the third piece 313 to keep the engagement portions 311, 315 apart so that the first and second pieces 310a, 313 may rotate relative to each other. The spring may be used in place of or in addition to spring 426 (FIG. 18). Upon moving a tightening device (e.g., nut 412, FIG. 18) towards the second clamp structure 304, the spring may be compressed and the engagement portions 311, 315 may contact each other. Once the engagement portions 311, 315 contact each other, the first and third pieces 310a, 313 may be prevented from rotating with respect to each other. Moreover, the third piece 313 may have a socket 317, which may be defined by a recessed surface 319 with a concave spherical contour. The recessed surface 319 may engage the outer bearing surface 378 (FIG. 18) similar to the manner in which the recessed surface 330 of the first piece 310 may engage the surface 378. The spring positioned between the first and third pieces 310a, 313 and/or the spring 426 may provide a spring force which may be sufficient to hold the convex bearing surface 378 against the concave bearing surface 319 in the socket 317 of the third piece 313. Such a construction may enable the concave bearing surface 319 and convex bearing surface 378 slide with respect to each other.

The second clamp structure 304 may also have two pieces 360 and 362. The first piece 360 (FIGS. 23 and 24) may have a cylindrical configuration which may be centered on an axis 365. Two inner surfaces 366 and 368 may define a passage 370, which may extend through the first piece 360. One of the inner surfaces 366 and 368 may be conical. The other may have a portion 372 shaped as a bearing surface with a concave spherical contour. In one embodiment, an enlarged end portion 376 of the first piece 360 may have an outer bearing surface 378 with a convex spherical contour. The first piece 360 may further have an external screw thread 380, which may extend axially from the end portion 376, and a pair of notches 382 which may receive a tool such as, for example, a screwdriver across the opposite side of the end portion 376. The notches 382 may enable the first piece 360 to be screwed tightly into the second piece 362.

FIG. 25 illustrates the second piece 362 of the second clamp structure 304. The second clamp structure may have a generally cylindrical configuration with a longitudinal axis 390. A screw-threaded counterbore 392 at one end of the second piece 362 may receive the first piece 360 as shown in FIG. 18. An aperture 393 may provide access to the threads 380 for deforming the screw thread 380 on the first piece 360 so as to fasten the two pieces 360 and 362 together. Those skilled in the art will appreciate that any configuration of the first and second pieces 360, 362 is envisioned so long as a connector (e.g., bolt 410) may be held within the second clamp structure 304. For example, in an embodiment where the opening 394 may be large enough to insert a connector (e.g., bolt 410) into the passage 370, the first and second pieces 360, 362 may be made of a single piece of material. In other embodiments, the first piece 360 and the second piece 362 may not have corresponding threads but may be attached by other methods such as, for example, welding, adhesive, press fitting, soldered, pinning.

An opening 394 may extend axially inward from the opposite end to receive the fixation element 306, as shown in FIG. 17. A bore 396, which may be at an angle (e.g. perpendicular) with respect to the longitudinal axis, may extend through the second piece 362 along an axis 397 and may intersect the bore 394. Moreover, a screw-threaded section 398, which may also be at an angle (e.g. perpendicular) with respect to the longitudinal axis, may extend through the second piece 362 along an axis 397 and may intersect the bore 394. The section 398 may be sized and configured to receive a set screw 400, which may retain a fixation element 306 within the opening 394. Bore 396 may be sized and configured to receive a tool, which may be used to deform the threads of the screw 400 positioned within section 398 such that the screw 400 may be prevented from being removed from the second piece 362. In one embodiment, a fixation element 306 may have a threaded end for threading into the section 398. Moreover, in another embodiment, the opening 394 may be threaded and may receive a set screw 400 so that a fixation element 306 may be positioned and held in bore 396 by the screw 400.

The clamp assembly 300 may also include a connector device in the form of a bolt 410 and a tightening device in the form of a nut 412, which may be screwed onto the bolt 410. The head 416 of the bolt 410 may be received in the passage 370 in the first piece 360 of the second clamp structure 304. A convex spherical bearing surface 418 on the head 416 may be seated in sliding contact with the concave inner bearing surface 372 in the passage 370. The bolt stem 420 may extend from the passage 370, through the openings 325 and 350 in the first clamp structure 302, and axially outward from the first clamp structure 302. The screw thread 422 on the bolt stem 420 may be deformed to prevent removal of the nut 412 from the bolt 410.

A ring 424 may be interposed between the first clamp structure 312 and the nut 412. A spring 426 may be captured between opposed pockets 428 and 430 in the ring 424 and the nut 412, respectively. In this arrangement, the spring 426 may be compressed axially between the first clamp structure 312 and the nut 412. This may provide a spring force which may be sufficient to hold the convex bearing surface 378 against the concave bearing surface 330 in the socket 328. Thus, the clamp assembly 300 may equipped with a spring-loaded mechanism which may be operative to apply a variable spring force to resist pivotal movement of the first and second clamp structures 302 and 304 relative to each other in the same manner as described above with reference to the clamp assemblies 10 and 200. Such a construction may enable the first and second clamp structures 302 and 304 to be provisionally held in a variety of fixed orientations relative to each other when the nut 412 is positioned a distance from the first clamps structure 302 and/or the ring 424. As the nut 412 is drawn closer to the first clamp structure 302, the first and second clamp structures 302 and 304 may be rigidly fixed in an orientation with respect to each other.

Figure 26:
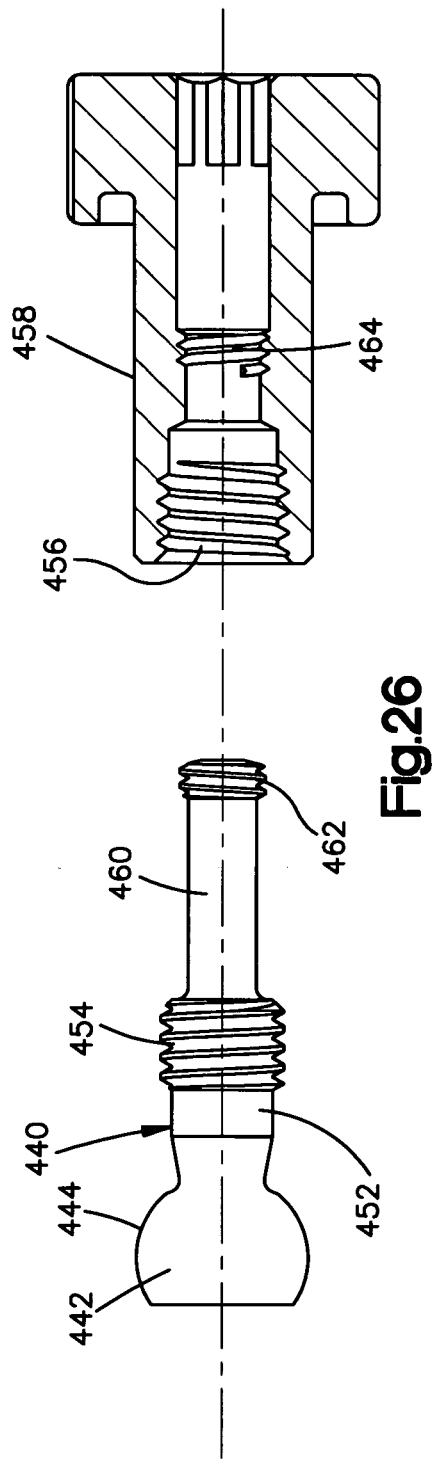
FIG. 26 is a sectional view of alternative parts of a clamp assembly.

FIG. 26 illustrates an alternative embodiment of a connector bolt 440 which may be used with any clamp described herein and, in particular, as an alternative to bolt 128 or connector 210. The connector bolt 440 may have a head 442 with a convex spherical bearing surface 444, and a stem 452 with a right-hand screw thread 454 which may engage with a right-hand screw thread 456 on a corresponding tightening device 458. A projecting portion 460 of the stem 452 may have an additional screw thread 462 at its terminal end. Screw thread 462 is preferably in a different direction from screw thread 454. The tightening device 458, which in this example is an elongated knob, may have an additional screw thread 464, which may correspond to screw thread 462. The additional screw threads 462 and 464 may be left-hand threads which may have diameters less than the diameters of the right-hand threads 454 and 456. In another embodiment, the threads 454 and 456 may be left-hand screw threads and threads 462 and 464 may be right-handed screw threads.

In use, the knob 458 may be installed on the bolt 440 by moving the left-hand thread 464 on the knob 458 axially into engagement with the left-hand thread 462 on the bolt 440, and by rotating the knob 458 in a counterclockwise direction so that the knob 458 may be advanced axially onto the bolt 440 (in a direction from right to left as viewed in FIG. 26). Further counterclockwise rotation of the knob 458 may move the left-hand thread 464 on the knob 458 axially past the left-hand thread 462 on the bolt 440. In this manner, the tightening device or knob 458 may be retained on the connector bolt 440. Moreover, the knob 458 is similar to tightening device 212. A spring may be provided around the connector bolt 440 and the knob 458 to provide tension between the clamp structures.

After the knob 458 has been installed on the bolt 440, the knob 458 may be moved axially back and forth on the bolt 440. If the knob 458 is moved axially along the shaft of the bolt 440, the right-hand thread 456 on the knob 458 may then be engaged with the right-hand thread 454 on the bolt 440. Thereafter, rotating the knob 458 may provide further axial movement of the knob 458 along the bolt 440 to apply a variable spring force in the manner described above with reference to, for example, the nut 130 and the tightening device 212. The left-hand threads 462 and 464 may help to prevent inadvertent removal of the knob 458 from the bolt 440 because they require the knob 458 to be rotated clockwise rather than counterclockwise as it is backed off of the bolt 440.

FIGS. 27-29 illustrate a device 500 which may be an assembly of fixation elements and which may be used with, for example, any one or more of the clamp assemblies 10, 200 and 300 described above. It will be appreciated by those skilled in the art that any other clamp may be used with the device 500 to form an external fixation system. This device 500 may include a connector block 502 and three fixation elements 504, 506 and 508. It should be noted, however, that the connector block 502 may be sized and configured to join two or more fixation elements. For example, the connector block 502 may be sized and configured to connect, for example, element 504 and 506, element 506 and 508, element 504 and 508 or four, five, or six fixation elements. The fixation elements 504, 506 and 508 may be straight or curved rods or bars. In FIG. 27-29 the connector block 502 and fixation element 504, 506 and 508 are shown illustratively in a T-shaped arrangement, with the first rod 504 having the greatest length and the second and third rods 506 and 508 may be equal in length to each other but lesser in length to the first rod 504. It will be appreciated that, in other embodiments, the first rod 504 may have a lesser length than one or both of the second and/or third rods 506, 508. In other embodiments, all the rods 504, 506 and 508 may have different lengths.

As shown in FIG. 28, the axes 511 and 513 of the second and third rods 506 and 508, respectively, may be at an angle (e.g., perpendicular) to the axis 515 of the first rod 504 in the T-shaped arrangement. Moreover, as shown in FIG. 29, the axes 511 and 513 of the second and third rods 506 and 508, respectively, may be at an angle A relative to each other. The angle A may be, for example, an obtuse angle between about 90 degrees and about 180 degrees and, most preferably, between about 140 degrees and about 160 degrees. Such a configuration may be an optimal arrangement for the device 500 which may be installed in a wrist-fixation frame. In a wrist-fixation frame, the first rod 504 may extend above and substantially parallel to the length of the forearm, and the second and third rods 506 and 508 may extend down towards the forearm and at an angle with respect to the length of the forearm (e.g., with the surface 502*a* facing away from the forearm). It should be recognized that the device 500 may be used with the clamp assemblies 10, 200 and 300 to create an external fixation frame anywhere on the body including, for example, the wrist, hand, feet, jaw, arm, leg and/or long bones.

The components of the device 500 may be made of the same or different material and may be made of, for example, metal (e.g., stainless steel, titanium, aluminum), plastic, rubber and alloy of two or more materials, or a composite material (i.e., made up of two or more materials). Moreover, the components of the device 500 may be radiolucent or radioopaque (e.g., carbon fiber). In one embodiment, the components of the device 500 may be made of radiolucent material with radioopaque markers.

As shown in FIG. 27, the first rod 504 may project longitudinally outward from a counterbore 520 in the connector block 502. A terminal end portion of the first rod 504 may be received within the counterbore 520 and may be secured in place by, for example, welding, press-fitting and/or an adhesive bonding. The second and third rods 506 and 508 may be fixed to the connector block 502 in the same manner so that all three rods 504, 506 and 508 may be permanently interconnected and immovable relative to each other. An articulated clamp assembly 10, 200 or 300 may be used to connect any one of the three rods 504, 506 and 508 to one or more fixation element, which may be angularly orientated with respect to the rods 504, 506 and/or 508 in an assembled external fixation frame.

Figure 30:
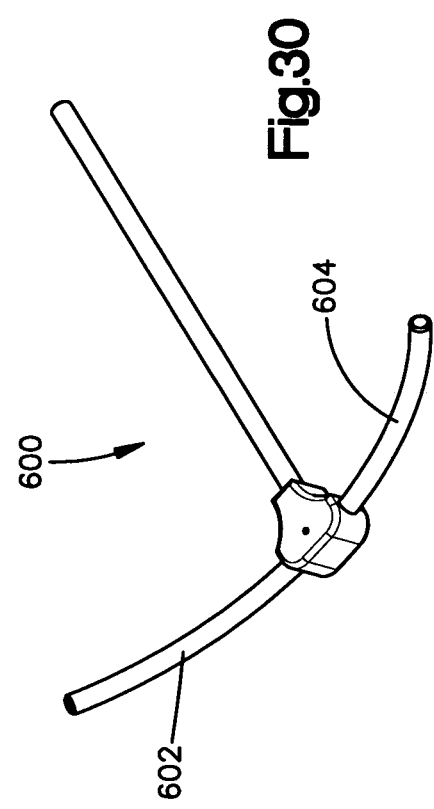
FIG. 30 is a view similar to FIG. 27, showing another assembly of bone fixation elements.

FIG. 30 illustrates a device 600 which is similar to the device 500. The device 600 may have a second and third fixation rods 602 and 604 which may be curved rather than straight. The curved rods 602 and 604 may have equal and concentric radii of curvature. In another embodiment, the radii of curvature may be different.

While the foregoing description and drawings represent the preferred embodiments of the present invention, it will be understood that various additions, modifications and substitutions may be made therein without departing from the spirit and scope of the present invention as defined in the accompanying claims. In particular, it will be clear to those skilled in the art that the present invention may be embodied in other specific forms, structures, arrangements, proportions, and with other elements, materials, and components, without departing from the spirit or essential characteristics thereof.

One skilled in the art will appreciate that the invention may be used with many modifications of structure, arrangement, proportions, materials, and components and otherwise, used in the practice of the invention, which are particularly adapted to specific environments and operative requirements without departing from the principles of the present invention. The presently disclosed embodiments are therefore to be considered in all respects as illustrative and not restrictive, the scope of the invention being indicated by the appended claims, and not limited to the foregoing description.

What is claimed is:

1. An apparatus for engaging first and second bone fixation elements in a bone fixation frame, comprising:
   a first clamp structure, having at least two bores for engaging at least two first bone fixation elements having a first spherically contoured bearing surface;
   a second clamp structure, having at least one bore for engaging at least one second bone fixation element, having a second spherically contoured bearing surface seated in sliding contact with the first bearing surface;
   a connector bolt having a head engaging the second clamp structure and a screw-threaded stem extending to the first clamp structure;
   a tightening device in screw-threaded engagement with the stem of the connector bolt; and
   a spring compressed between the first clamp structure and the tightening device, whereby the tightening device can apply a spring force to the connector bolt to tighten the contact of the bearing surfaces by moving the bearing surfaces toward one another.

2. An apparatus as defined in claim 1 wherein the tightening device is rotatable relative to the connector bolt so as to vary compression of the spring by moving along the connector bolt relative to the spring and the first clamp structure.

3. An apparatus as defined in claim 1 wherein the connector bolt and the first clamp structure are free of a key that blocks rotation of the connector bolt relative to the first clamp structure.

4. An apparatus as defined in claim 1 wherein the connector bolt and the tightening device are together configured to block disengagement of the tightening device from the connector bolt.

5. An apparatus as defined in claim 1 wherein the tightening device has a flexible locking portion configured to snap into interlocked engagement with the connector bolt upon moving along the connector bolt.

6. An apparatus as defined in claim 1 wherein the stem of the connector bolt has a right-hand screw thread and a left-hand screw thread, and the tightening device has a corresponding right-hand screw thread and a corresponding left-hand screw thread.

7. An apparatus as defined in claim 1 wherein the bearing surface on one of the clamp structures is concave and engages the other bearing surface circumferentially to an extent that is insufficient to capture the other clamp structure.

8. An apparatus as defined in claim 1 wherein the first bearing surface is concave and the second bearing surface is convex.

9. An apparatus as defined in claim 1 wherein the first clamp structure comprises two opposed pieces that together define a channel configured to receive the first bone fixation element between the two opposed pieces.

10. An apparatus as defined in claim 1 wherein the second clamp structure is a unitary part consisting of a single body of material.

11. An apparatus as defined in claim 1 wherein the second clamp structure comprises an elongated body with a ball end defining the second bearing surface.

12. An apparatus as defined in claim 1 wherein the second clamp structure has a part with the second bearing surface and a different part configured to engage the second bone fixation element.

13. An apparatus as defined in claim 1 wherein the first clamp structure is configured to engage more than one bone fixation element, and the second clamp structure is configured to engage only one bone fixation element.

14. An apparatus as defined in claim 1 further comprising first and second fasteners configured to fasten the first and second bone fixation elements to the first and second clamp structures, respectively.

15. An apparatus as defined in claim 14 wherein the first and second fasteners are set screws.

16. An apparatus as defined in claim 1 wherein the first clamp structure is a unitary part consisting of a single body of material.

* * * * *